United States Patent
Serafin, Jr. et al.

(10) Patent No.: US 9,308,674 B1
(45) Date of Patent: Apr. 12, 2016

(54) IMPLANT BODY WITH RING

(75) Inventors: Louis A. Serafin, Jr., Lakeport, MI (US); Nicholas H. Burlingame, Belmont, NY (US); Gerald J. Jerry, Jr., St. Clair, MI (US)

(73) Assignees: Signal Medical Corporation, Marysville, MI (US); Gerald J. Jerry, Jr., St. Clair, MI (US)

( * ) Notice: Subject to any disclaimer, the term of this patent is extended or adjusted under 35 U.S.C. 154(b) by 1684 days.

(21) Appl. No.: 11/401,395

(22) Filed: Apr. 10, 2006

Related U.S. Application Data

(60) Provisional application No. 60/676,667, filed on Apr. 29, 2005.

(51) Int. Cl.
| | | |
|---|---|---|
| A61F 2/28 | (2006.01) | |
| A61F 2/32 | (2006.01) | |
| A61F 2/34 | (2006.01) | |
| B29C 31/02 | (2006.01) | |

(52) U.S. Cl.
CPC .................................... B29C 31/02 (2013.01)

(58) Field of Classification Search
USPC ............ 623/22.19, 22.2, 22.29, 23.24, 23.25, 623/22.28, 22.32, 22.33
See application file for complete search history.

(56) References Cited

U.S. PATENT DOCUMENTS

| | | | | |
|---|---|---|---|---|
| 3,347,465 | A | * | 10/1967 | Shieber .................... 239/265.11 |
| 4,166,292 | A | * | 9/1979 | Bokros ...................... 623/21.18 |
| 5,049,158 | A | * | 9/1991 | Engelhardt et al. ........ 623/22.25 |
| 5,549,691 | A | * | 8/1996 | Harwin ...................... 623/22.37 |
| 5,549,700 | A | * | 8/1996 | Graham et al. ............ 623/22.14 |
| 5,755,807 | A | * | 5/1998 | Anstaett et al. ............. 623/22.2 |
| 5,989,293 | A | | 11/1999 | Cook et al. ..................... 623/22 |
| 6,162,256 | A | * | 12/2000 | Ostiguy et al. ............ 623/22.26 |
| 6,224,633 | B1 | * | 5/2001 | Kalberer et al. ........... 623/22.24 |
| 6,231,612 | B1 | * | 5/2001 | Balay et al. ............... 623/22.31 |
| 6,319,285 | B1 | * | 11/2001 | Chamier et al. ........... 623/22.32 |
| 6,368,354 | B2 | * | 4/2002 | Burstein et al. ............ 623/22.28 |
| 6,416,553 | B1 | * | 7/2002 | White et al. ............... 623/22.38 |
| 7,267,693 | B1 | * | 9/2007 | Mandell et al. ............ 623/22.28 |
| 2002/0006532 | A1 | * | 1/2002 | Robin .......................... 428/697 |
| 2003/0050705 | A1 | * | 3/2003 | Cueille et al. ............. 623/22.24 |
| 2004/0054418 | A1 | * | 3/2004 | McLean et al. ............ 623/22.17 |
| 2005/0246031 | A1 | * | 11/2005 | Frederick et al. .......... 623/22.29 |

OTHER PUBLICATIONS

Serafin, Jr., et al., U.S. Appl. No. 60/676,667 filed Apr. 29, 2005 A.D.
Portland Orthopaedics > Products > Equator Plus Cup, web pages (www.margron.com/m_p_eqplus.htm) downloaded May 23, 2006.

* cited by examiner

*Primary Examiner* — Yashita Sharma
(74) *Attorney, Agent, or Firm* — Christopher John Rudy

(57) ABSTRACT

Implant body has a groove into which an outer ring is fitted. The body and ring are distinct solid parts both during and after assembly. A "flat" wall may be provided for the groove. The outer ring is annularly continuous and may be under tension, with the body under correspondent compression from the ring. An arthroplasty device can be provided.

21 Claims, 1 Drawing Sheet

IMPLANT BODY WITH RING

This claims benefits under 35 USC 119(e) of provisional application No. 60/676,667 filed on Apr. 29, 2005 A.D. The specification of that application is incorporated herein by reference in its entirety.

FIELD AND PURVIEW OF THE INVENTION

The present invention concerns an implant body having an outer ring. For an illustrative example, the body may be an acetabular cup such as of a ceramic or composite, say, a ceramic, e.g., a Magnesium oxide containing, transformationally toughened zirconia (MgO-TTZ), and the ring of metal, say, of a Titanium alloy, e.g., 6-4-1 ELI, about an outer circumference of the cup.

BACKGROUND TO THE INVENTION

Various hip implant components are known. Among these are acetabular cups.

In one such cup, provided as an ensemble, an ultra high molecular weight polyethylene (UHMWPE) cup insert is positioned in a metal shell through an internally biased retaining ring on the shell that engages a corresponding annular groove on the cup insert. The cup insert may have a hood and recessed stops about a circumference of its lip for "dialing in" the hooded insert with respect to a surgically implanted shell that has corresponding upraised post stops on its rim for engaging the recessed stops of the cup insert. The shell may have a porous or mesh outer coating for bonding with bone of the surgically prepared acetabular socket of the patient.

One problem with such an ensemble revolves around the UHMWPE. Many practitioners understand UHMWPE, as useful and desirable as it is, especially in total joint prostheses, to form wear debris particles, which over the course of time after implantation may engender osteolysis and aseptic loosening of the implant.

Accordingly, metal or, even better, ceramic, is often proposed to replace the UHMWPE.

However, replacing an UHMWPE insert with ceramic is not always a simple exchange.

In another such cup, a ceramic cup, the body is provided as one piece. A roughened outer surface such as from grinding it to be rough or from adding a metal porous coating such as from metal vapor deposition may be provided to help bond the implant to the bone stock of the prepared acetabulum of the patient. In the former case bone ingrowth often insufficiently occurs, necessitating the use of surgical cement, which itself may fail over time, and in the latter case it may be desirable to avoid a sputtered metal coating on the ceramic cup because of cost and other considerations.

Another arrangement may provide a taper on an outer surface of the cup onto which a correspondingly tapered ring may be fitted. Such an arrangement is not without its drawbacks.

Nevertheless, it remains desirable to improve the instant art, noting especially the ever present desire of surgeons and their patients for better and better joint implant performance.

A FULL DISCLOSURE OF THE INVENTION

In general, provided is an implant body with a groove into which an outer ring is fitted.

The invention is useful in arthroplasty.

Significantly, by the invention, the art is improved in kind. More particularly, highly biocompatible and durable ceramic or composite implant bodies can be adapted to be reliably made part of ensembles with metal shells, and the use of UHMWPE can be avoided if desired. A porous or mesh metal coating for engendering bone ingrowth on a ceramic or composite cup can be provided, and the use of metallic vapor deposition can be avoided. Moreover, when a ring such as a metal ring is bound in tension about a circumference of the cup, particularly in ceramics, increased strength can result. Such a ring may be provided on a plastic cup, say, on UHMWPE. Also, the ring may be of a ceramic or composite, or a plastic, say, of UHMWPE. The system can incorporate the latest in materials which can provide for such fulfillments in the lacks and needs of the art.

Numerous further advantages attend the invention.

BRIEF SUMMARY OF THE DRAWINGS

The drawings form part of the specification hereof. With respect to the drawings, which are not necessarily drawn to scale, the following is briefly noted.

ADDITIONAL DETAIL

Figure 1:
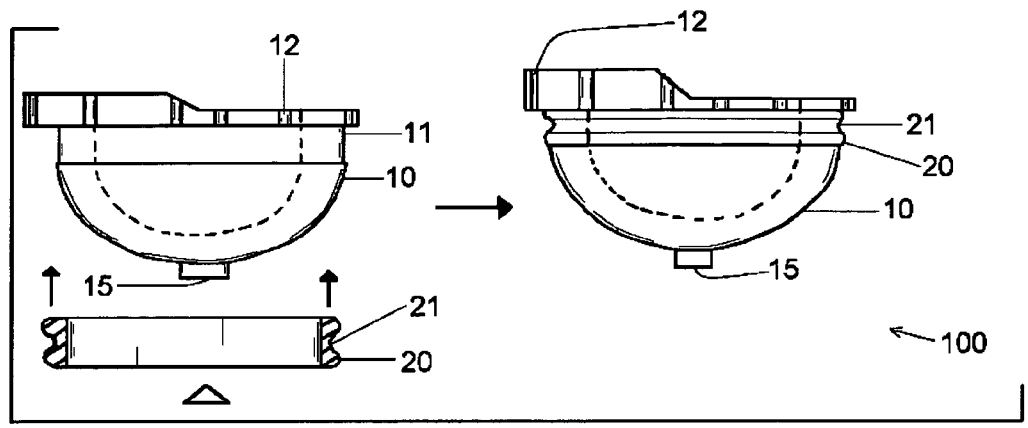
FIG. 1 shows an implant body cup insert having an outer ring of the invention for a total enarthrodial type replacement joint implant, and its manufacture, embodied as a total hip replacement implant cup insert.

The invention can be further understood by the additional detail set forth below. The same is to be taken in an illustrative and not necessarily limiting sense.

The invention embraces an implant body having an outer ring.

For instance, the implant body may be a cup or cup insert for an enarthrodial joint implant such as for the hip, shoulder, digits, and so forth. The body has in combination with it the outer ring. The implant body has, in general, an outer circumference in which a groove can be provided, which preferably is shallow. The ring is provided in the groove, advantageously, under tension, with the body under correspondent compression.

Preferably, the implant body is hard.

As a hard implant body, one or more of a ceramic, composite, metal and/or alloy, and so forth may be employed. In general, for a prosthetic implant, the hard substance is biocompatible. Preferably, the hard substance is ceramic.

As the ceramic, ceramics from "A" to "Z" may be mentioned, to include alumina and zirconia ceramics. Thus, such ceramics can include those known in the art and those described by Serafin, Jr., et al., in International patent publication No. WO 2004/080340. In ceramics, in general, certain zirconia ceramics have demonstrated improvement over alumina. High quality zirconia can often be polished to a better surface finish than alumina. It is stronger, tougher and yet easier to machine when finished than alumina. It therefore can be a more versatile material with which to design, but alumina is not necessarily debilitating. However, as disclosed by Serafin, Jr., et al. above, the ceramic can be machined green and then fired to yield a final ceramic implant product with little if any machining. Of the zirconia ceramics, a magnesium oxide (MgO) stabilized transformationally toughened zirconia (TTZ) having about from two to five percent by weight MgO, for example, about from 3.1 to 3.4 wt. % MgO, may be beneficially employed, say, to make a glenoid or acetabular cup or cup insert.

As the composite, any suitable composite may be employed.

As the metal and/or alloy may be mentioned Titanium metal and its alloys (Ti-alloys) such as 6-4-1 ELI, Cobalt metal and its alloys such as containing Cobalt-Chromium (Co—Cr), and stainless steel. Other suitable metals and/or alloys may be employed.

As alluded to above, zirconia ceramics are a preferred type of ceramic. The excellent mechanical properties of TTZ ceramics and the range of ceramic alloys that can be formed allow tailoring these materials for specific part requirements. A zirconia based alloy system can be employed to advantage. Zirconia alloys are much stronger than alumina. Additionally, these materials generally have lower elastic moduli, which would increase contact areas (decrease contact stress) by approximately 50% over an alumina system. Additionally, the zirconia based system is very versatile; by varying the amount and type of alloy additives and heat treatments, a range of properties can be obtained. The materials selected can be from zirconia alloys similar to those which are presently used for femoral heads and acetabular cups. For example, Mg-PSZ, MgO-TTZ, or Y-TZP based materials may be employed. The MgO-TTZ ceramic is preferred.

Although they may not be hard in comparison to a metal, composite, or ceramic, and even though their use may otherwise be avoided, the implant body may embrace a plastic such as a polyolefin, to include the UHMWPE, a nylon, a polyurethane, and so on. The ring, too, may even be composed of such a plastic if desired.

As the ring, any suitable substance may be employed. Accordingly, a suitable ceramic, composite, metal or alloy, or even plastic may be employed. Advantageously, however, the ring is composed of the metal or alloy, among which can be mentioned again Titanium and Ti-alloys such as 6-4-1 ELI; Cobalt and its alloys such as Co—Cr, and stainless steel. A Ti-alloy is beneficially employed as the ring, especially in combination with a ceramic implant body.

With respect to the drawings, device 100 includes implant body 10 and outer ring 20. The device 100 may be an implant component typically requiring additional part(s) such as backing shell 30 to enhance or utilize its functionality (FIGS. 1, 2) or an implant component generally not requiring such additional part(s) (FIG. 3).

The body 10, for example, of MgO-TTZ ceramic, may be in a form of a cup, for example, an acetabular cup insert or cup. It may include ring-receiving groove 11 (FIG. 1), which may be very slight indeed, or, instead of the groove 11, a simple "flat" wall that may be circumferential and of the same dimension as the more rounded portion of the body 10 adjacent it (FIG. 3). Alignment notch(es) 12 may be provided about a perimeter of a lip of the cup insert, and may include a hood (FIGS. 1, 2), or stop notch 12' may be provided as an interruption in an otherwise annular protrusion 14 below a lip of the cup (FIG. 3) or a plurality of such interruptions, say, two that oppose each other in a 180-degree relationship, or that have an asymmetric alignment orientation. Stabilizing rear button 15 may be provided in, for example, the cup insert (FIGS. 2, 3).

Figure 2:
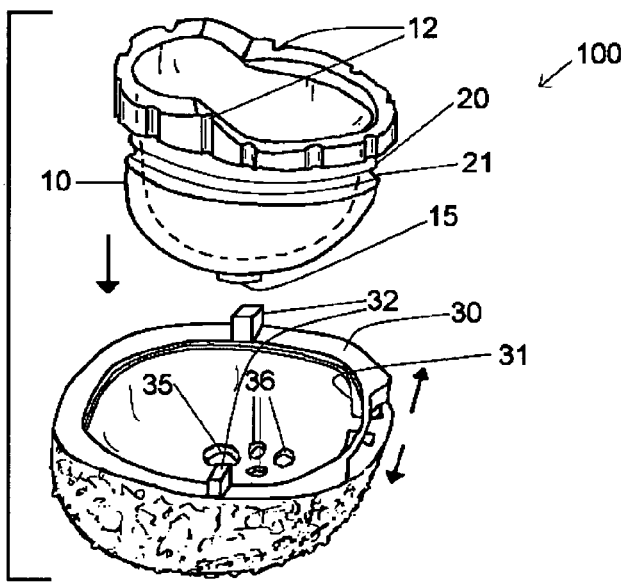
FIG. 2 shows an ensemble combining a metal shell and the cup insert of FIG. 1.
Figure 3:
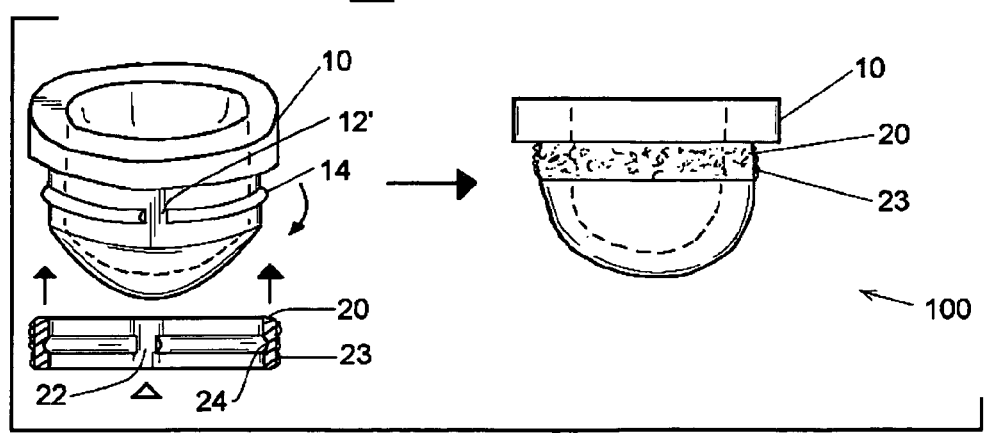
FIG. 3 shows an implant body cup having an outer ring of the invention for a total enarthrodial type replacement joint implant, and its manufacture, embodied as a total hip replacement implant cup. Such a cup can be implanted without employment of a metal shell.

The ring 20, for example, of 6-4-1 ELI Ti-alloy, can be adapted for employment as part of an ensemble, and include a ring body having outer groove 21 (FIGS. 1, 2). As an alternative, the ring 20 can be adapted for combination with a body 10 that can function as a stand alone implant component, and include a ring body, which may have inner stop 22 for matching up with the stop notch 12'; outer porous or mesh coating 23 for engendering bone ingrowth; and inner groove 24 for fitting closely over the protrusion 14 (FIG. 3).

The ring 20 is attached to the body in any suitable manner. Preferably, the ring 10 has a coefficient of expansion significantly different, for instance, greater, than that of the body 20. With application of heat and/or cold to either or both the ring 20 or body 10, for example, heating only a metal ring 10, the ring 10 is put onto the body 10. When both parts 10/20 reach ambient temperature, the ring 20 is secured about the body 10, beneficially quite tightly (FIGS. 1, 3).

The shell 30, for example, of 6-4-1 Ti-alloy, can include inwardly biased spring ring 31 for receipt in the groove 21; alignment posts 32 for receipt in selected opposing notches 12; porous or mesh outer coating 33 for engendering bone ingrowth; blind hole 35 for receiving the button 15; and holes 36 for employing bone screws. When the shell 30 is implanted, spreading the ring 31 with tabs can release the insert 10/20 for removal or realignment of the hood.

CONCLUSION

The present invention is thus provided. Various features, parts, steps subcombinations or combinations can be employed with or without reference to other features, parts, steps, subcombinations and combinations in the practice of the invention, and numerous adaptations and modifications can be effected within its spirit, the literal claim scope of which is particularly pointed out as follows:

What is claimed is:

1. An arthroplasty device comprising, assembled, as distinct, solid parts both during and after assembly of the arthroplasty device therewith:
   a hard implant body of ceramic with a continuous circumferential groove about an outer portion of the implant body; and
   an outer ring, which is annularly continuous and fitted into the continuous circumferential groove of the implant body to reside there to provide the arthroplasty device;
   such that the outer ring is restrained from rotation in the continuous circumferential groove, and is bound under tension against the implant body to provide increased strength to the implant body.

2. The arthroplasty device of claim 1, wherein the outer ring is a metal or metal alloy, wherein, with the outer ring bound under tension against the implant body, the implant body is under correspondent compression from the outer ring, such that the outer ring is secured tightly about the implant body from the tension and compression.

3. The arthroplasty device of claim 2, which provides a cup for an enarthrodial joint implant.

4. The arthroplasty device of claim 3, wherein the outer ring includes an outer circumferential groove, and the device further comprises a backing shell to which the assembled implant body and outer ring attach through the outer circumferential groove of the outer ring.

5. The arthroplasty device of claim 2, wherein the outer ring includes an outer porous surface.

6. The arthroplasty device of claim 3, wherein the outer ring includes an outer porous surface.

7. The arthroplasty device of claim 1, wherein the ceramic is MgO-TTZ.

8. The arthroplasty device of claim 2, wherein the ceramic is MgO-TTZ.

9. The arthroplasty device of claim 3, wherein the ceramic is MgO-TTZ.

10. The arthroplasty device of claim 4, wherein the ceramic is MgO-TTZ.

11. The arthroplasty device of claim 5, wherein the ceramic is MgO-TTZ.

12. The arthroplasty device of claim 6, wherein the ceramic is MgO-TTZ.

13. An arthroplasty device comprising, assembled, as distinct, solid parts both during and after assembly of the arthroplasty device therewith:
   an implant body with a continuous circumferential groove about an outer portion of the implant body; and
   an outer ring, which is annularly continuous and fitted into the continuous circumferential groove of the implant body to reside there to provide the arthroplasty device;
such that the outer ring is restrained from rotation in the continuous circumferential groove; and which further comprises:
   in the continuous circumferential groove of the implant body, at least one stop notch provided as an interruption in an otherwise annular protrusion in the continuous circumferential groove; and
   in the outer ring, at least one inner stop matching up with the at least one stop notch provided as an interruption in an otherwise annular protrusion in the continuous circumferential groove of the implant body, and an inner groove for fitting closely over the otherwise annular protrusion in the continuous circumferential groove of the implant body.

14. An arthroplasty device comprising, assembled, as distinct, solid parts both during and after assembly of the arthroplasty device therewith:
   a hard implant body of ceramic in a form of a cup, with a circumferential, simple, substantially flat wall about an outer portion of the implant body, which is of the same outer dimension as a convexly rounded portion of the implant body immediately adjacent it; and
   an outer ring, which is annularly continuous and fitted onto the circumferential simple substantially flat wall of the implant body and bound under tension against the implant body that is under correspondent compression from the outer ring so as to provide increased strength to the implant body and reside there to provide the arthroplasty device, which is useful in arthroplasty.

15. The arthroplasty device of claim 14, wherein the outer ring is a metal or metal alloy.

16. The arthroplasty device of claim 15, wherein the assembled implant body with outer ring provides a cup insert for an enarthrodial joint implant, and which has alignment notches about a perimeter of a lip of the cup.

17. The arthroplasty device of claim 14, wherein the ceramic is MgO-TTZ.

18. The arthroplasty device of claim 15, wherein the ceramic is MgO-TTZ.

19. The arthroplasty device of claim 16, wherein the ceramic is MgO-TTZ.

20. An arthroplasty device comprising, assembled, as distinct, solid parts both during and after assembly of the arthroplasty device therewith:
   an implant body with a circumferential, substantially flat wall about an outer portion of the implant body, which is of the same outer dimension as a convexly rounded portion of the implant body immediately adjacent it; and
   an outer ring, which is annularly continuous and fitted onto the circumferential, substantially flat wall of the implant body to reside there to provide the arthroplasty device,
which further comprises:
   in the circumferential, substantially flat wall about an outer portion of the implant body, at least one stop notch provided as an interruption in an otherwise annular protrusion in the circumferential, substantially flat wall; and
   in the outer ring, at least one inner stop matching up with the at least one stop notch provided as an interruption in an otherwise annular protrusion in the circumferential, substantially flat wall of the implant body, and an inner groove for fitting closely over the otherwise annular protrusion in the circumferential, substantially flat wall of the implant body.

21. The arthroplasty device of claim 20, which is an acetabular cup.

\* \* \* \* \*